(12) United States Patent
Giarelli et al.

(10) Patent No.: US 11,980,696 B1
(45) Date of Patent: May 14, 2024

(54) HYPOCHLOROUS ACID MEDICAL PROBE DISINFECTION CHAMBER

(71) Applicant: Disinfection Technology Solutions LLC, Mentor, OH (US)

(72) Inventors: Nick Giarelli, Mentor, OH (US); Marc Piscitelli, Winter Garden, FL (US)

(73) Assignee: Disinfection Technology Solutions LLC, Mentor, OH (US)

( * ) Notice: Subject to any disclaimer, the term of this patent is extended or adjusted under 35 U.S.C. 154(b) by 0 days.

(21) Appl. No.: 17/686,769

(22) Filed: Mar. 4, 2022

(51) Int. Cl.
    *A61L 2/22* (2006.01)
    *A61L 2/025* (2006.01)

(52) U.S. Cl.
    CPC ............... *A61L 2/22* (2013.01); *A61L 2/025* (2013.01); *A61L 2202/122* (2013.01); *A61L 2202/15* (2013.01); *A61L 2202/24* (2013.01)

(58) Field of Classification Search
    CPC .... A61L 2/22; A61L 2202/24; A61L 2202/17; A61L 2202/122; A61L 2202/15; A61L 2202/121; A61L 2/025; A61L 9/14; A61L 2202/123; A61L 2209/15; A61L 2202/12; A61L 12/026
    USPC .......................................................... 422/28
    See application file for complete search history.

(56) References Cited

U.S. PATENT DOCUMENTS

| | | | | |
|---|---|---|---|---|
| 5,225,160 A * | 7/1993 | Sanford | ............... | B65D 77/225 422/1 |
| 5,529,750 A * | 6/1996 | Kochte | ............... | A61L 2/18 134/102.1 |
| 5,807,521 A * | 9/1998 | Franetzki | ............... | A61L 2/07 422/128 |
| 5,980,462 A * | 11/1999 | Maruta | ............... | A61B 8/4461 600/462 |
| 6,013,227 A * | 1/2000 | Lin | ............... | A61L 2/186 422/305 |
| 6,162,395 A * | 12/2000 | Kowanko | ............... | A61L 2/208 422/294 |
| 6,558,620 B1 * | 5/2003 | Sanford | ............... | A61B 1/123 134/102.2 |
| 6,582,654 B1 * | 6/2003 | Kral | ............... | A61B 1/125 134/171 |
| 6,596,232 B1 * | 7/2003 | Lin | ............... | A61L 2/186 134/22.12 |
| 6,641,781 B2 * | 11/2003 | Walta | ............... | A61B 50/10 134/92 |
| 7,249,773 B2 | 7/2007 | Schreiber et al. | | |
| 7,824,608 B2 * | 11/2010 | Kuroshima | ............... | A61L 2/24 422/105 |

(Continued)

*Primary Examiner* — David G Cormier
*Assistant Examiner* — Thomas Bucci
(74) *Attorney, Agent, or Firm* — Renner, Otto, Boisselle & Sklar, LLP

(57) ABSTRACT

A disinfection chamber for disinfecting probe and probe cord may include a housing, a probe chamber portion defined by the housing, a cord chamber portion defined by the housing, one or more disinfecting portions in operable communication with the probe chamber portion and the cord chamber portion, and a disinfectant composition in operable communication with the one or more disinfecting portions. The one or more disinfecting portions may expel the disinfectant composition within the probe chamber portion and the cord chamber portion to disinfect the probe and at least a portion of the probe cord.

19 Claims, 7 Drawing Sheets

(56) References Cited

U.S. PATENT DOCUMENTS

| | | | |
|---|---|---|---|
| 8,196,604 B1* | 6/2012 | Ricciardi | A61L 9/14 251/74 |
| 8,529,833 B2 | 9/2013 | Morgantini et al. | |
| 8,840,733 B2* | 9/2014 | Komiya | B08B 9/027 134/169 C |
| 9,333,275 B2 | 5/2016 | Berentsveig | |
| 10,188,764 B2 | 1/2019 | Cunningham | |
| 10,675,369 B1* | 6/2020 | Ricciardi | A61L 2/084 |
| 11,241,513 B1* | 2/2022 | Ricciardi | B65B 5/04 |
| 2005/0025671 A1* | 2/2005 | Kral | A61L 2/20 422/62 |
| 2005/0025685 A1* | 2/2005 | Selig | A61L 2/20 422/292 |
| 2005/0025686 A1* | 2/2005 | Sargent | A61L 2/18 422/301 |
| 2007/0154371 A1* | 7/2007 | Lin | A61B 1/125 422/300 |
| 2008/0295277 A1* | 12/2008 | Onishii | A61L 2/18 15/302 |
| 2009/0090398 A1* | 4/2009 | Onishi | A61L 2/025 134/167 C |
| 2010/0022839 A1* | 1/2010 | Onishi | A61B 1/123 600/158 |
| 2010/0071736 A1* | 3/2010 | Watanabe | A61B 1/125 134/56 R |
| 2010/0140134 A1* | 6/2010 | Deshays | A61L 2/26 206/702 |
| 2010/0140342 A1* | 6/2010 | Deshays | A61B 90/98 235/375 |
| 2011/0223075 A1* | 9/2011 | Berentsveig | A61L 2/22 422/292 |
| 2012/0308956 A1* | 12/2012 | DeVengencie | A61C 17/20 433/119 |
| 2013/0152982 A1* | 6/2013 | Tanaka | A61B 90/70 134/115 R |
| 2014/0166059 A1* | 6/2014 | Kosugi | A61B 1/00128 134/113 |
| 2014/0290700 A1* | 10/2014 | Langford | A61B 90/70 134/22.12 |
| 2015/0297769 A1* | 10/2015 | Dobbyn | G01R 3/00 134/99.1 |
| 2016/0081540 A1* | 3/2016 | Suzuki | A61B 1/00059 134/56 R |
| 2016/0302654 A1* | 10/2016 | Ogawa | B08B 9/023 |
| 2016/0324997 A1* | 11/2016 | Dayton | A61L 2/10 |
| 2017/0172397 A1* | 6/2017 | Zardini | A61B 1/125 |
| 2018/0332877 A1* | 11/2018 | Tak | A23L 3/32 |
| 2019/0142985 A1 | 5/2019 | Cunningham | |
| 2019/0151485 A1* | 5/2019 | Song | A61C 19/00 |
| 2020/0254124 A1* | 8/2020 | Baumgartner | B05B 17/0615 |
| 2021/0402025 A1* | 12/2021 | Kuzniar | B08B 7/0057 |

\* cited by examiner

HYPOCHLOROUS ACID MEDICAL PROBE DISINFECTION CHAMBER

BACKGROUND

There is a need in the field for improvements to conventional disinfection systems to make them more safe, cost-effective, convenient, and widely available.

SUMMARY OF THE INVENTION

The present disclosure may provide a disinfection chamber for disinfecting a probe and at least a portion of a probe cord. The probe, such as, for example, an ultrasound probe, may be enclosed within a probe chamber portion and at least a portion of the cord may be enclosed within a cord chamber portion. The disinfection chamber may expel a safe disinfectant composition (e.g., a disinfectant composition that is non-toxic to humans) within the enclosed probe chamber portion and the enclosed cord chamber portion to disinfect the probe and the cord respectively. As such, the disinfection chamber may be used for disinfecting or sterilizing probes and probe cords thereby eliminating all microorganisms, or a suitable level of microorganisms, on the probes and probe cords.

This is beneficial compared to conventional disinfection systems as conventional disinfection systems may use toxic or unsafe disinfectant compositions and only disinfect a probe leaving the probe cord to be disinfected manually, if at all.

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1:
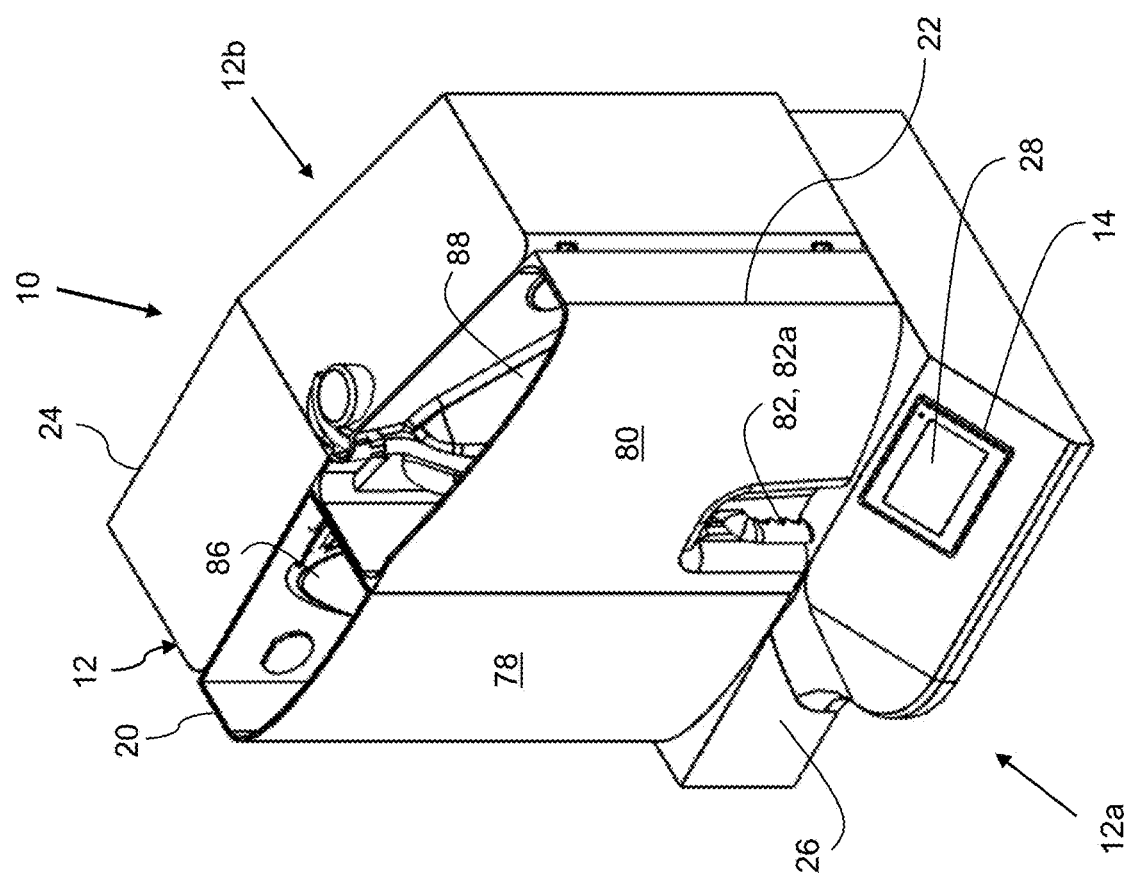
FIG. 1 illustrates a perspective view of an exemplary disinfection chamber in accordance with one aspect of the present disclosure.
Figure 2:
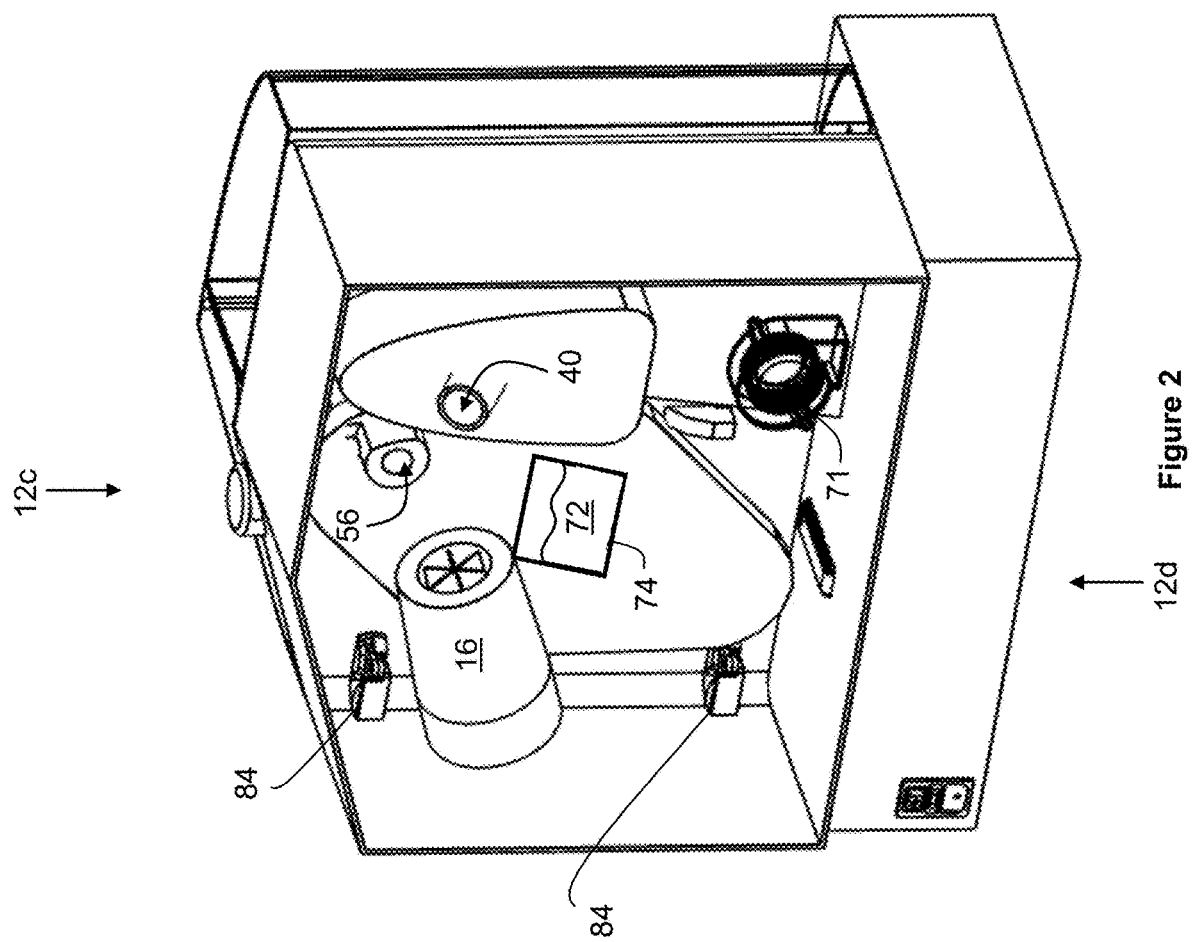
FIG. 2 illustrates a rear perspective view of the exemplary disinfection chamber.

FIG. 1 through FIG. 6 illustrate an exemplary disinfection chamber 10 for disinfecting a probe 1 and its associated probe cord 3. The probe 1 and its associated cord 3 may be any type of probe having any type of cord, such as, for example, an ultrasound probe having an associated ultrasound probe cord.

The disinfection chamber 10 may include a housing 12, a controller 14, and a waste removal assembly 16. The housing 12 may include a front 12a, a rear 12b, a top 12c, a bottom 12d, a first side 12e, and a second side 12f. The front 12a and the rear 12b may define a transverse direction therebetween. The top 12c and the bottom 12d may define a vertical direction therebetween. The first side 12e and the second side 12f may define a longitudinal direction therebetween. The housing 12 may further include a probe chamber portion 20, a cord chamber portion 22, a rear portion 24, and a base 26.

The controller 14 may be provided within the base 26 of the housing 12 and may include a user interface 28. An exemplary controller 14 may be a combination of a human machine interface and a programmable logic controller (PLC) that allows a user to program and/or operate the disinfection chamber as more fully described below.

The probe chamber portion 20 may include a probe chamber surface 30 and a securing mechanism 32. The probe chamber surface 30 may define a recessed probe receiving cavity 34 and a recessed probe transition cavity 36. The securing mechanism 32 may be a clip that releasably secures the probe 1 within the probe receiving cavity 34.

Figure 6:
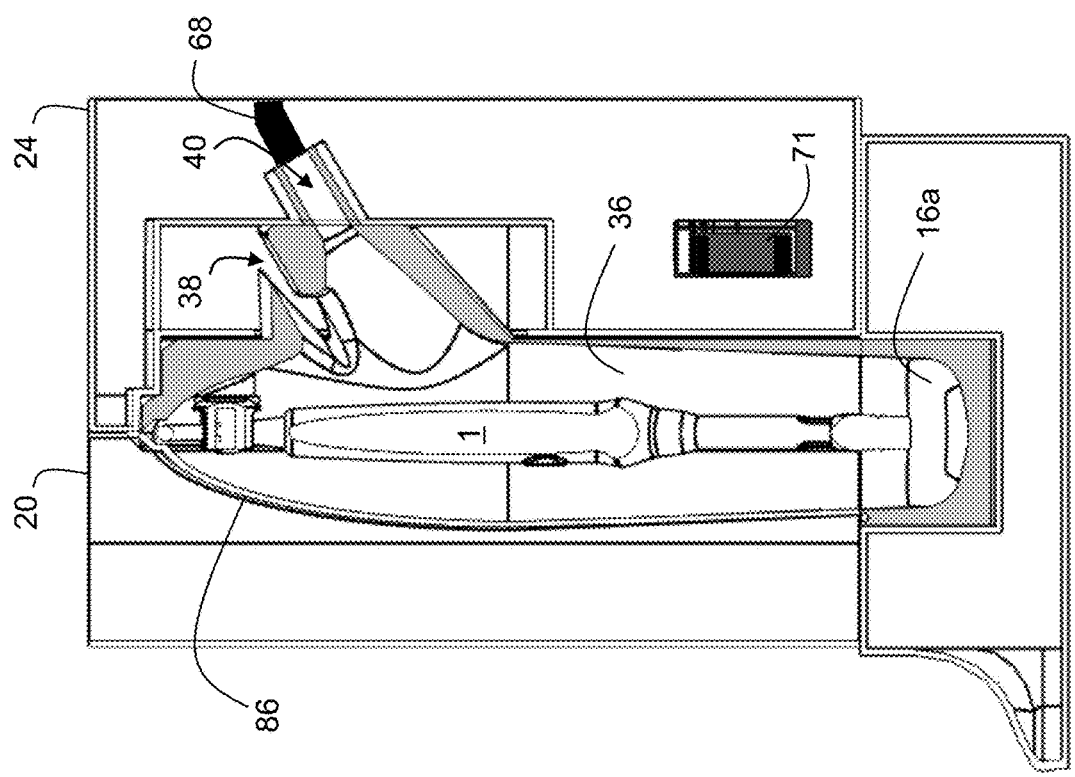
FIG. 6 is a cross section view looking in the direction of line 6-6 of FIG. 4.
Figure 7:
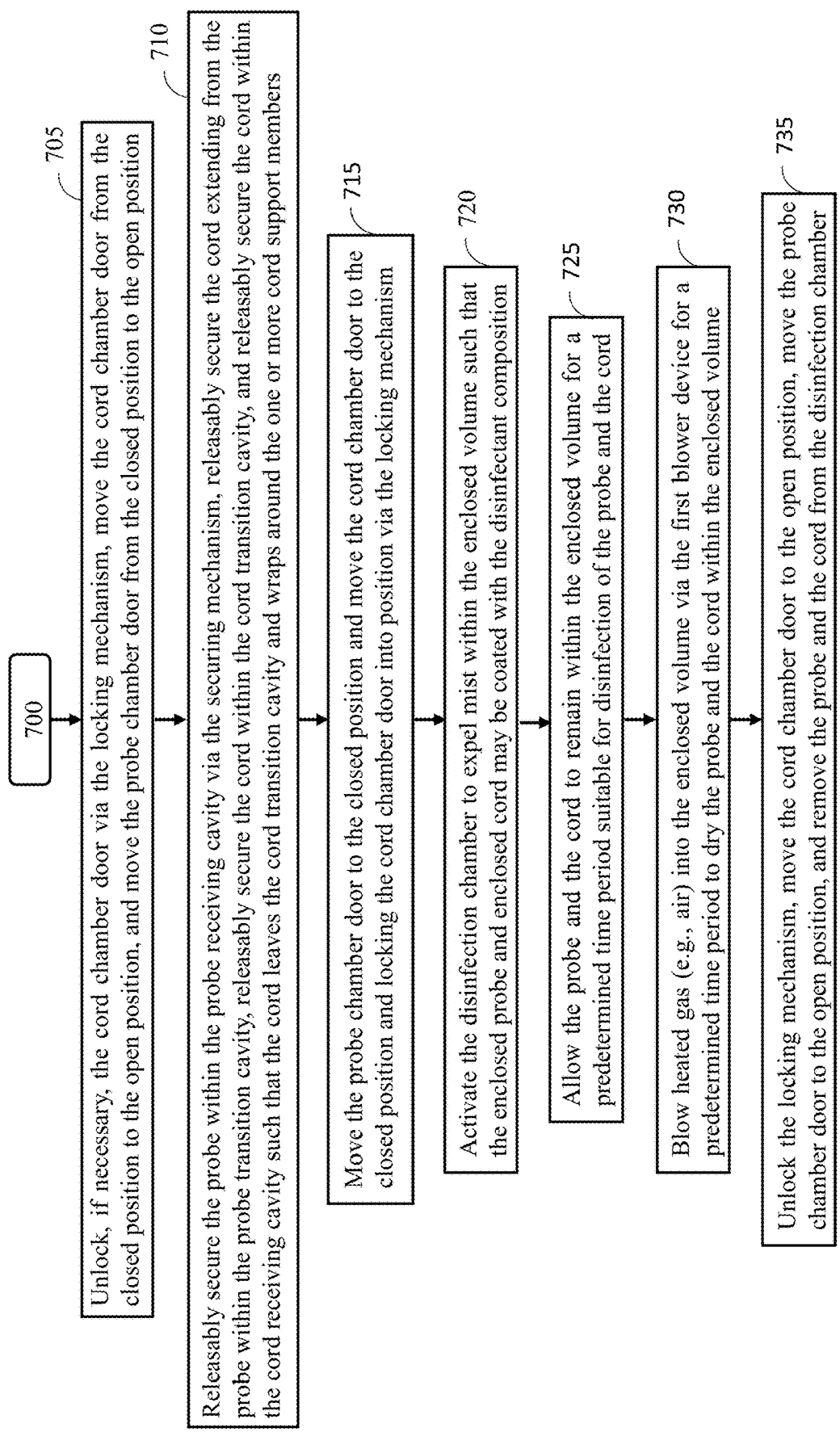
FIG. 7 illustrates a flow diagram for an exemplary method for disinfecting a probe and a probe cord.

The probe receiving cavity 34 may be in operable communication with the probe transition cavity 36 and the probe receiving cavity 34 may transition to the probe transition cavity 36 at a probe transition point 37. The probe receiving cavity 34 may releasably receive the probe 1 and the probe transition cavity 36 may releasably receive a portion of the cord 3. The probe receiving cavity 34 may define a first aperture 38 and a second aperture 40 extending therethrough (FIG. 6). The probe receiving cavity 34 may take on a substantially inverted rounded V-shape and the probe transition cavity 36 may be provided proximate the top 12c of the disinfection chamber 10 and may extend from the probe receiving cavity 34 in a generally longitudinal direction toward the first side 12e of the disinfection chamber 10.

The cord chamber portion 22 may include a cord chamber surface 42 and one or more cord support members 44. The cord chamber surface may define a recessed cord receiving cavity 48 and a recessed cord transition cavity 50. The cord receiving cavity 48 may be in operable communication with the cord transition cavity 50 and the cord receiving cavity 48 may transition to the cord transition cavity 50 at a cord transition point 51. The cord receiving cavity 48 and the cord transition cavity 50 may each releasably receive a portion of the cord 3. The cord receiving cavity 48 may define a first aperture 52, a second aperture 54, and a third aperture 56. The cord receiving cavity 48 may take on a substantially rounded diamond shape and may include a first curve portion 58, a second curve portion 60, a third curve portion 62, and a fourth curve portion 64. The first curve portion 58 and the second curve portion 60 may be coplanar with one another and the third curve portion 62 and the fourth curve portion 64 may be coplanar with one another.

A first axis X1 may extend through an approximate midpoint of the first curve portion 58 and the second curve portion 60 and a second axis X2 may extend through an approximate midpoint of the third curve portion 62 and the fourth curve portion 64. The first axis X1 and the second axis X2 may intersect with one another at a center point 66 of the substantially diamond shaped cord receiving cavity 48.

The one or more cord support members 44 may be elongated members engaged with the cord receiving cavity 48 such that the one or more cord support members 44 extend in a transverse direction toward the front 12a of the housing 12. In some implementations, the one or more cord support members 44 may include a first cord support member 44a, a second cord support member 44b, a third cord support member 44c, a fourth cord support member 44d, a fifth cord support member 44e, a sixth cord support member 44f, a seventh cord support member 44g, an eighth cord support member 44h, a ninth cord support member 44i, and a tenth cord support member 44j arranged in a particular configuration. For example, the first cord support member 44a may be positioned proximate the cord transition point 51 and between the first aperture 52, the second aperture 54, and the third aperture 56. The remaining nine cord support members 44b, 44c, 44d, 44e, 44f, 44g, 44h, 44i, and 44j may be positioned along the along the first axis X1 and the second axis X2.

In particular, the second cord support member 44b and the sixth cord support member 44f may be positioned along the second axis X1 such that the second cord support member 44b is spaced a distance from the sixth cord support member 44f with the second cord support member 44b being closer to the fourth curve portion 64, the third cord support member 44c, the seventh cord support member 44g, and the tenth cord support member 44j may be positioned along the first axis X1 such that the third cord support member 44c, the seventh cord support member 44d and the tenth cord support member 44j are spaced a distance from one another with the third cord support member 44c being closest to the second curve portion 60 and the seventh cord support member 44g being closer to the second curve portion 60 than the tenth cord support member 44j, the fourth cord support member 44d and the eighth cord support member 44h may be positioned along the second axis X2 such that the fourth cord support member 44d is spaced a distance from the eighth cord support member 44h with the fourth cord support member 44d being closer to the third curve portion 62, and the fifth cord support member 44e and the ninth cord support member 44i may be positioned along the first axis X1 such that the fifth cord support member 44e is spaced a distance from the ninth cord support member 44i with the fifth cord support member 44e being closer to the first curve portion 58.

The first cord support member 44a, the second cord support member 44b, the third cord support member 44c, the fourth cord support member 44d, and the fifth cord support member 44e may each have a substantially similar first length, the sixth cord support member 44f, the seventh cord support member 44g, the eighth cord support member 44h, and the ninth cord support member 44i may each have a substantially similar second length, and the tenth cord support member 44j may have a third length. The first length may be less than the second length and the third length and the second length may be less than the third length.

Figure 4:
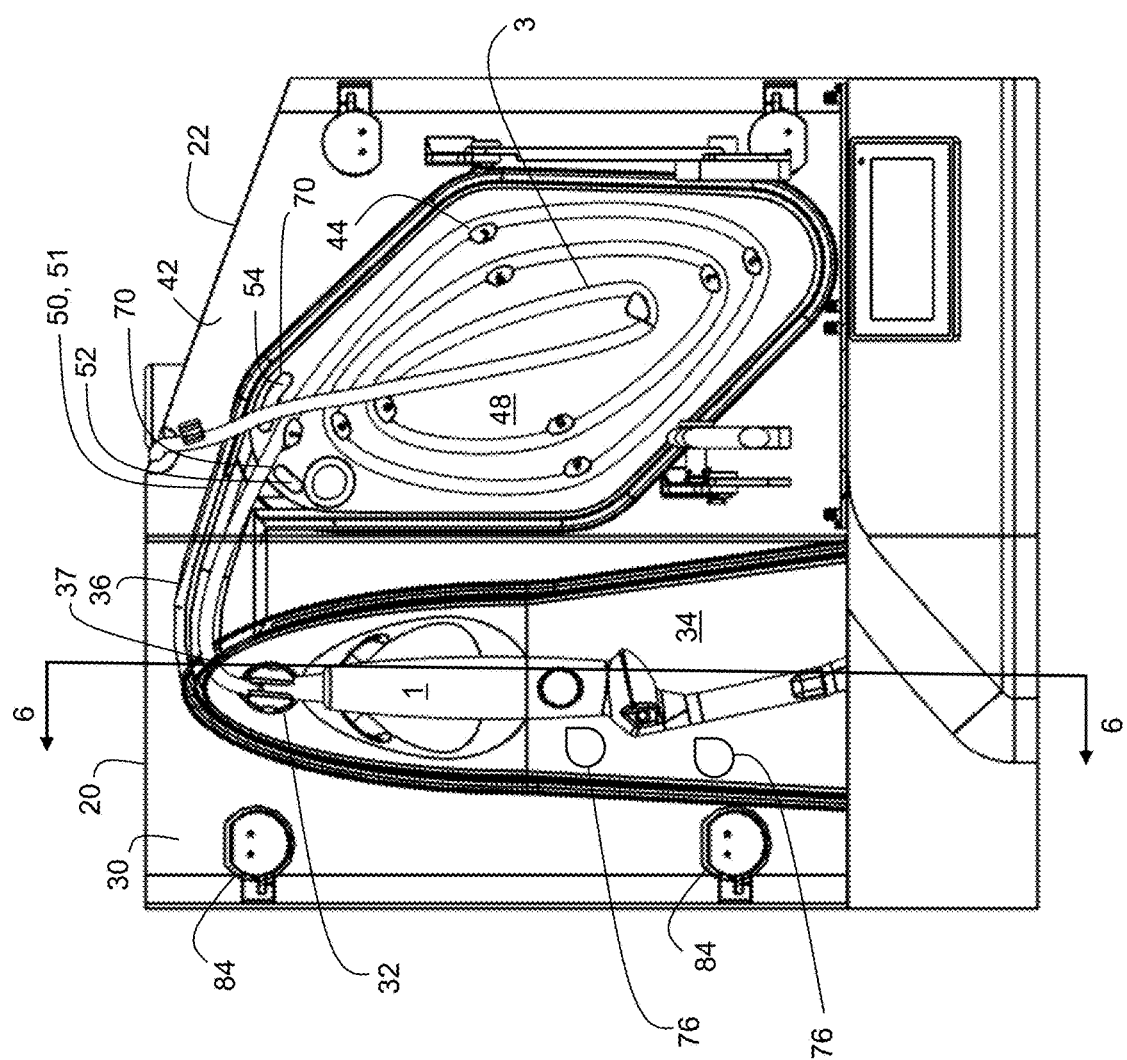
FIG. 4 illustrates a cross section view looking in the direction of line 4-4 of FIG. 3.
Figure 5:
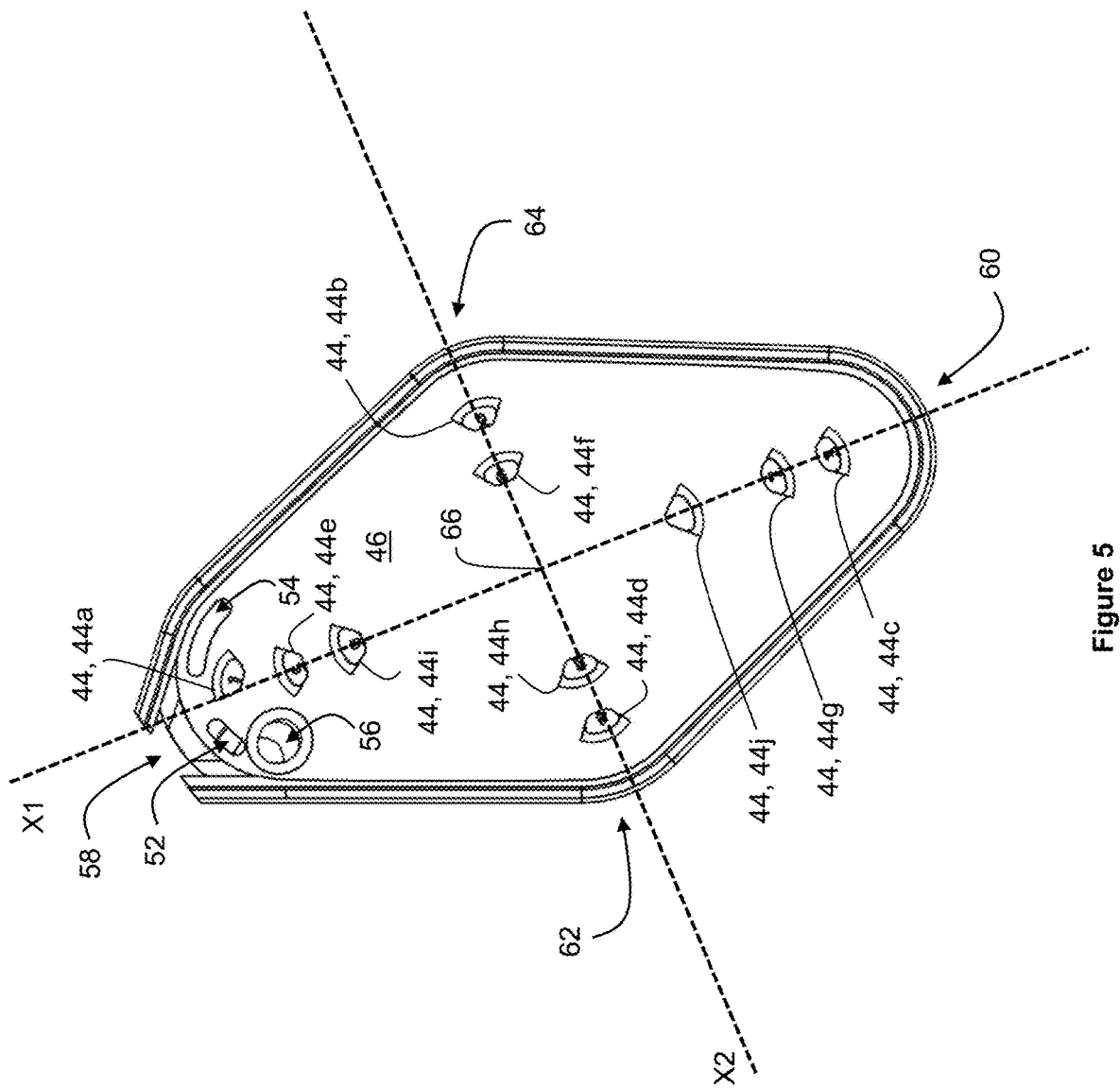
FIG. 5 is an isolated view of an exemplary cord receiving cavity in accordance with one aspect of the present disclosure.

The disinfection chamber 10 may further include a probe disinfecting portion 68 (FIG. 6), a cord disinfecting portion 70 (FIG. 4). In some implementations, the probe disinfecting portion 68 and the cord disinfecting portion 70 may be ultrasonic nebulizers, such as, for example, piezoelectric nebulizers. As such, the probe disinfecting portion 68 and the cord disinfecting portion 70 may be in operable communication with a heated blower 71 and a disinfectant composition 72 being stored within a disinfectant composition storage container 74. The probe disinfecting portion 68 may be in fluid communication with the probe chamber portion 20 via the second aperture 40 (FIG. 6) of the probe receiving cavity 34 and the cord disinfecting portion 70 may be in fluid communication with the cord chamber portion 22 via the third aperture 56 (FIG. 2) of the cord receiving cavity 48. The first aperture 38 of the probe receiving cavity 34, the second first aperture 52 of the cord receiving cavity 48, and the second aperture 54 of the cord receiving cavity 48 may serve as vents allowing suitable pressurization of the probe chamber portion 20 and the cord chamber portion 22.

The disinfectant composition 72 may be electrolyzed water, which is produced by electrolyzing water containing dissolved sodium chloride (e.g., tap water). In particular, the reaction products may be a solution of hypochlorous acid (HOCl) and sodium hydroxide (NaOH) and the solution may be used as a disinfectant. Exemplary benefits of using electrolyzed water as a disinfectant solution is that it is non-toxic to humans. In some implementations, a potential of hydrogen (pH) of the disinfectant composition 72 may be between a range of 4.8 and 5.2; however, it is to be understood that the pH of the disinfectant composition 72 may be any suitable pH.

The probe disinfecting portion 68, the cord disinfecting portion 70, the heated blower 71, the disinfectant composition 72, and the disinfectant composition storage container 74 may operate to generate droplets 76 of the disinfectant composition 72 to be expelled within the probe chamber portion 20 (through the second aperture 40) and the cord chamber portion 22 (through the third aperture 56), respectively.

In some implementations, the probe disinfecting portion 68 may expel the droplets 76 in the form of a mist within the probe chamber portion 20 to disinfect the probe 1 and the cord disinfecting portion 22 may expel the droplets 76 in the form of a mist within the cord chamber portion 22 to disinfect the cord 3. The droplets 76 generated by the probe disinfecting portion 68 and the cord disinfecting portion 70 may have a size in a range from twelve microns to forty microns.

As the probe disinfecting portion 68 and the cord disinfecting portion 70 may use vibration to generate and expel the droplets 76, the size of the droplets 76 may be adjusted based, at least in part, on a frequency of the vibration used by the probe disinfecting portion 68 and the cord disinfecting portion 70. Stated otherwise, the size of the droplets 76 may be controlled as desired by changing the frequency of the vibration associated with the probe disinfecting portion 68 and the cord disinfecting portion 70.

While the probe disinfecting portion 68 has been described as being in fluid communication with the probe chamber portion 20 via the second aperture 40 and the cord disinfecting portion 70 as being in fluid communication with the cord receiving cavity 48 via the third aperture 56, it is to be understood that the probe disinfecting portion 68 and the cord disinfecting portion 70 may be provided in any suitable location within the housing 12 to be in fluid communication with the probe chamber portion 20 and the cord chamber portion 22, respectively.

The waste removal assembly 16 may include one or more waste reservoirs 16a and one or more waste evacuation devices (not shown) for collecting disinfectant composition 72 waste within the probe chamber portion 20 and the cord chamber portion 22 and evacuating the collected disinfectant composition 72 waste from within the probe chamber portion 20 and from within the cord chamber portion 22.

The disinfection chamber 10 may further include a probe chamber door 78, a cord chamber door 80, and a locking mechanism 82. The probe chamber door 78 may selectively enclose the probe receiving cavity 34 and the probe transition cavity 36 and the cord chamber door 80 may selectively enclose the cord receiving cavity 48 and the cord transition cavity 50.

Figure 3:
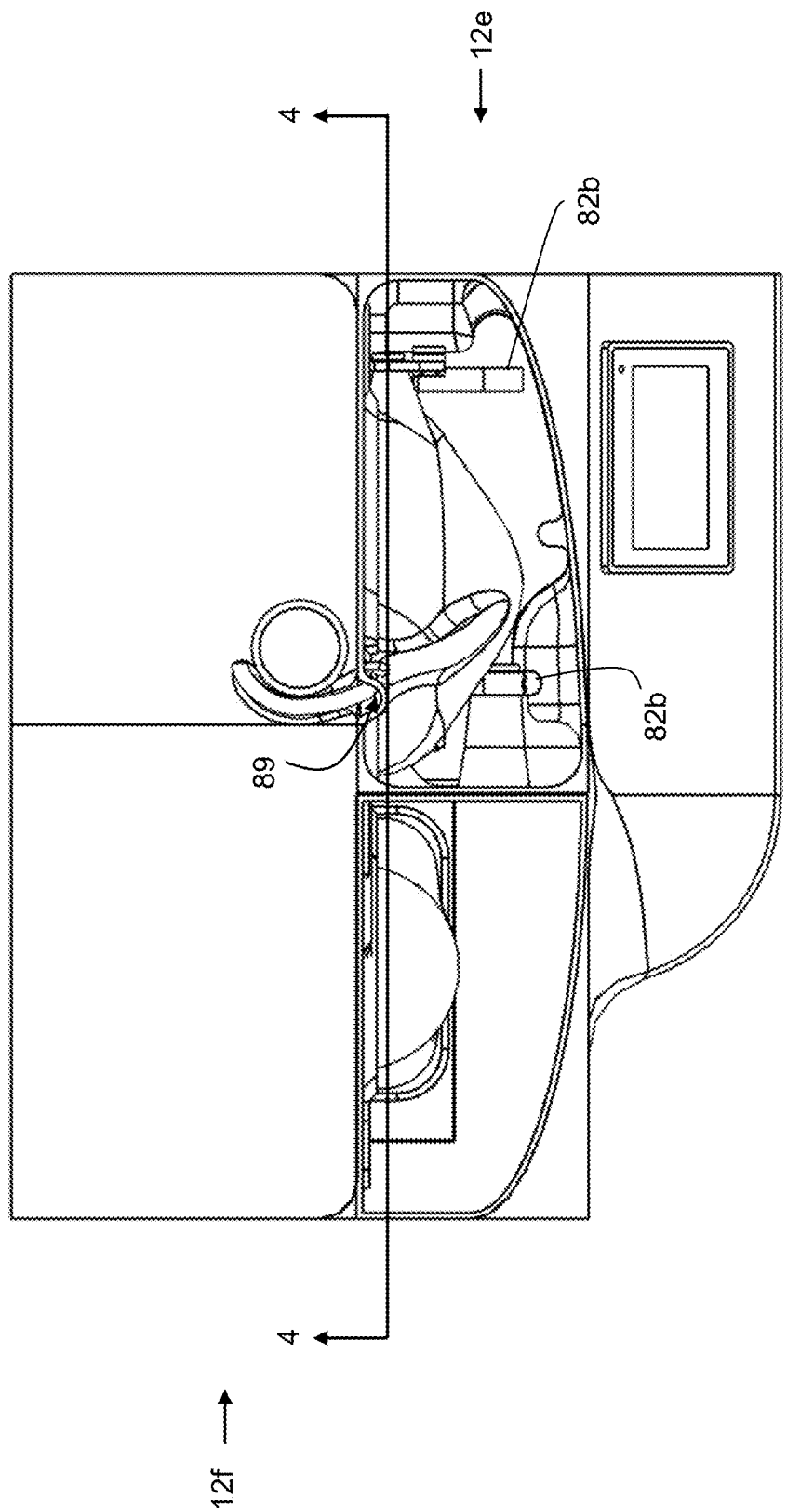
FIG. 3 illustrates a top plan view of the exemplary disinfection chamber.

The probe chamber door 78 and the cord chamber door 80 may be operably engaged with the housing via hinges 84. The probe chamber door 78 may define a probe enclosing portion 86 and the cord chamber door 80 may define a cord enclosing portion 88 therein and an exit aperture 89 (FIG. 3). The exit aperture 89 may be provided proximate the top 12c of the housing 12 and may allow a portion of the cord 3 to pass therethrough. The probe enclosing portion 86 may be complementary in shape to the probe receiving cavity 34 and the probe transition cavity 36 and the cord enclosing portion 88 may be complementary in shape to the cord receiving cavity 48 and the cord transition cavity 50.

The probe chamber door 78 may be moveable between an open position and a closed position. As such, the probe chamber door 78 may be moved to the open position to allow access to the probe receiving cavity 34 and the probe transition cavity 36 and may be moved to the closed position to enclose the probe receiving cavity 34 and the probe transition cavity 36. The cord chamber door 80 may be moveable between an open position and a closed position. As such, the cord chamber door 80 may be moved to the open position to allow access to the cord receiving cavity 48 and the cord transition cavity 50 and may be moved to the closed position to enclose the cord receiving cavity 34 and the probe transition cavity 36.

The locking mechanism 82 may include a handle 82a and a linkage assembly 82b. The locking mechanism 82 may be operably engaged with the cord chamber door 80. The locking mechanism 82 may be moveable between a locked position and an unlocked position to lock and unlock the cord chamber door 80.

FIG. 8 illustrates a flow diagram for an exemplary method for disinfecting a probe 1 and its associated cord 3. At 705, the method 700 may include unlocking, if necessary, the cord chamber door via the locking mechanism, moving the cord chamber door from the closed position to the open position, and moving the probe chamber door from the closed position to the open position. At 710, the method 700 may include releasably securing the probe 1 within the probe receiving cavity via the securing mechanism, releasably securing a portion of the cord extending from the probe within the probe transition cavity, releasably securing a portion of the cord within the cord transition cavity, and releasably securing a portion of the cord within the cord receiving cavity such that the cord passes from the cord transition cavity and wraps around the one or more cord support members. In some implementations, the cord may be wrapped around the one or more cord support members in an ordered manner, such as, for example, around the first cord support member, the second cord support member, the third cord support member, the fourth cord support member, the fifth cord support member, the sixth support cord member, the seventh support cord member, the eighth support cord member, the ninth support cord member, and, finally, around the tenth cord support member.

At 715, the method 700 may include moving the probe chamber door to the closed position to form an enclosed volume within the probe chamber portion (i.e., the probe may be enclosed between the probe receiving cavity and the enclosing portion of the probe chamber door and a portion of the cord extending from the probe may be enclosed between the probe transition cavity and the enclosing portion of the probe chamber door), and moving the cord chamber door to the closed position (locking the cord chamber door into position via the locking mechanism) to form an enclosed volume within the cord chamber portion (i.e., a portion of the cord extending from the probe transition cavity may be enclosed between the cord transition cavity and the enclosing portion of the cord chamber door, the portion of the cord wrapped around the one or more cord support members may be enclosed between the cord receiving cavity and the enclosing portion of the cord chamber door, and a remaining portion of the cord may pass through the exit aperture 89 and out of the enclosed space).

At 720, the method 700 may include activating the disinfection chamber to expel mist within the enclosed volumes such that the enclosed probe and enclosed cord portions may be coated with the disinfectant composition. For example, a user may activate the disinfection chamber via the display (e.g., a touch screen display) to generate the droplets of disinfectant composition (e.g., electrolyzed water), via the probe disinfecting portion and the cord disinfection portion, and to expel the generated droplets as a mist (i.e., the droplets may have a size in the range of 12 microns to forty microns) within the enclosed volume such that the probe and cord may be coated with the mist.

The probe disinfecting portion and the cord disinfecting portion may expel the mist within the enclosed volumes such that the enclosed probe and the enclosed portions of the cord may be coated with the mist for a predetermined time period, such as, for example, eight minutes, ten minutes, or any other suitable period of time allowing disinfection or sterilization of the probe and portions of the cord. The probe disinfecting portion and the cord disinfecting portion may expel the mist within the enclosed volumes continuously, periodically, or in any other suitable manner.

At 725, the method 700 may allow the probe and the cord to remain within the enclosed volume for a predetermined time period suitable for disinfection of the probe and the cord. At 730, after the predetermined time period has elapsed, the method 700 may blow heated gas (e.g., air with no disinfectant composition) into the enclosed volume via the heated blower 71 for a predetermined time period to dry the probe and the cord within the enclosed volume. At 735, the method 700 may unlock the locking mechanism, move the cord chamber door to the open position, move the probe chamber door to the open position, and remove the probe and the cord from the disinfection chamber.

DEFINITIONS

The following includes definitions of selected terms employed herein. The definitions include various examples or forms of components that fall within the scope of a term and that may be used for implementation. The examples are not intended to be limiting. Both singular and plural forms of terms may be within the definitions.

As used herein, an "operable connection" or "operable coupling," or a connection by which entities are "operably connected" or "operably coupled" is one in which the entities are connected in such a way that the entities may perform as intended. An operable connection may be a direct connection or an indirect connection in which an intermediate entity or entities cooperate or otherwise are part of the connection or are in between the operably connected entities. In the context of signals, an "operable connection," or a connection by which entities are "operably connected," is one in which signals, physical communications, or logical communications may be sent or received. Typically, an operable connection includes a physical interface, an electrical interface, or a data interface, but it is to be noted that an operable connection may include differing combinations of these or other types of connections sufficient to allow operable control. For example, two entities can be operably connected by being able to communicate signals to each other directly or through one or more intermediate entities like a processor, operating system, a logic, software, or other entity. Logical or physical communication channels can be used to create an operable connection.

While example systems, methods, and so on, have been illustrated by describing examples, and while the examples have been described in considerable detail, it is not the intention of the applicants to restrict or in any way limit scope to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A disinfection chamber for disinfecting a medical probe including a probe cord, comprising:
   a housing;
   a probe chamber portion defined by the housing, the probe chamber portion having a probe receiving cavity configured to house the medical probe;
   a cord chamber portion defined by the housing, the cord chamber portion having a cord receiving cavity configured to house a majority of the probe cord of the medical probe, the cord receiving cavity being distinct from the probe receiving cavity;
   one or more disinfecting portions in operable communication with the probe chamber portion and the cord chamber portion;
   a disinfectant in operable communication with the one or more disinfecting portions; wherein the one or more disinfecting portions introduce the disinfectant within the probe chamber portion and the cord chamber portion to disinfect the probe and a majority of the probe cord surface;
   one or more cord support members provided within the cord chamber portion, the one or more cord support members extending in a transverse direction toward a front of the housing and including at least a first cord support member, a second cord support member, and a third cord support member, the first cord support member extending farther in the transverse direction than the second cord support member and the second cord support member extending farther in the transverse direction than the third cord support member such that the majority of the probe cord surface is exposed to the disinfectant introduced within the cord chamber portion;
   a probe transition cavity; and
   a cord transition cavity;
   wherein the probe transition cavity and the cord transition cavity define a passageway between the probe receiving cavity and the cord receiving cavity.

2. The disinfection chamber of claim 1, wherein the cord chamber portion is complementary in shape to at least a part of the majority of the probe cord, the at least a part of the majority of the probe cord being wrapped around the one or more cord support members.

3. The disinfection chamber of claim 1, further comprising:
   a cord chamber surface of the cord chamber portion; and
   a cord receiving cavity defined by the cord chamber surface.

4. The disinfection chamber of claim 3, further comprising:
   a probe chamber surface of the probe chamber portion;
   wherein the probe transition cavity is defined by the probe chamber surface;
   wherein the cord transition cavity is defined by the cord chamber surface; and
   wherein the probe transition cavity and the cord transition cavity are in operable communication with one another.

5. The disinfection chamber of claim 3, further comprising:
   a probe chamber surface of the probe chamber portion;
   wherein the probe transition cavity is defined by the probe chamber surface; and
   wherein the cord transition cavity is defined by the cord chamber surface; wherein a part of the majority of the probe cord is releasably received within the cord receiving cavity, the cord transition cavity, and the probe transition cavity.

6. The disinfection chamber of claim 1, wherein the disinfectant is electrolyzed water.

7. The disinfection chamber of claim 1, wherein the one or more disinfecting portions are ultrasonic nozzles.

8. The disinfection chamber of claim 1, wherein the disinfectant is introduced as a mist of droplets.

9. The disinfection chamber of claim 8, wherein a size of the droplets is in a range from twelve microns to forty microns.

10. A method for disinfecting a medical probe and a probe cord of the medical probe, comprising:
    arranging the medical probe within a probe receiving cavity in a probe chamber portion of a housing of a disinfection chamber;
    arranging a majority of the probe cord within a cord receiving cavity in a cord chamber portion of the housing of the disinfection chamber, at least the cord chamber portion having a door;
    arranging a portion of the probe cord within a cord transition cavity and a probe transition cavity wherein the portion of the probe cord is distinct from the majority of the probe cord, and wherein the probe transition cavity and the cord transition cavity define a passageway between the probe receiving cavity and the cord receiving cavity;
    introducing, via one or more disinfecting portions of the disinfection chamber, a disinfectant within the probe chamber portion and the cord chamber portion to disinfect the probe and a majority of the probe cord surface; and holding at least a part of the majority of the probe cord around one or more cord support members provided within the cord chamber portion, the one or more cord support members extending in a direction transverse to the door, the holding including contacting a first portion of the probe cord to a first cord support member and contacting a second portion of the probe cord to a second cord support member, the first cord support member extending in the transverse direction to a first plane and the second cord support member extending in the transverse direction to a second plane different from the first plane such that the majority of the probe cord surface is exposed to the disinfectant introduced within the cord chamber portion .

11. The method of claim 10, further comprising:
closing the door to enclose the majority of the probe cord between an enclosing portion of the door and the cord chamber portion.

12. The method of claim 10, further comprising:
arranging the majority of the probe cord within the cord receiving cavity;
wherein the cord receiving cavity is defined by a cord chamber surface.

13. The method of claim 10, further comprising:
releasably securing the majority of the probe cord within the cord receiving cavity defined by a cord chamber surface of the cord chamber portion, within the cord transition cavity defined by the cord chamber surface, and within the probe transition cavity defined by a probe chamber surface of the probe chamber portion.

14. The method of claim 13, wherein the probe transition cavity and the cord transition cavity are in operable communication with one another.

15. The method of claim 10, further comprising:
using electrolyzed water as the disinfectant.

16. The method of claim 10, further comprising:
using ultrasonic nozzles as the one or more disinfecting portions.

17. The method of claim 10, further wherein the disinfectant is introduced as a mist of droplets.

18. The method of claim 17, wherein a size of the droplets is in a range from twelve microns to forty microns.

19. The method of claim 10, the holding including contacting a third portion of the probe cord to a third cord support member, the third cord support member extending in the transverse direction to a third plane different from the first plane and the second plane.

* * * * *